US010391484B2

(12) United States Patent
Ledden et al.

(10) Patent No.: US 10,391,484 B2
(45) Date of Patent: Aug. 27, 2019

(54) SAMPLE DELIVERY SYSTEM

(71) Applicant: Siemens Healthcare Diagnostics Inc., Tarrytown, NY (US)

(72) Inventors: David J. Ledden, Medway, MA (US); Janine A. Cox, Stoughton, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 15/317,726

(22) PCT Filed: Jun. 11, 2015

(86) PCT No.: PCT/US2015/035326
§ 371 (c)(1),
(2) Date: Dec. 9, 2016

(87) PCT Pub. No.: WO2015/191853
PCT Pub. Date: Dec. 17, 2015

(65) Prior Publication Data
US 2017/0113217 A1  Apr. 27, 2017

Related U.S. Application Data

(60) Provisional application No. 62/011,609, filed on Jun. 13, 2014.

(51) Int. Cl.
*G01N 1/00* (2006.01)
*B01L 3/00* (2006.01)
*B01L 3/02* (2006.01)
*A61B 5/15* (2006.01)
(Continued)

(52) U.S. Cl.
CPC ........ *B01L 3/502* (2013.01); *A61B 5/150022* (2013.01); *A61B 5/150343* (2013.01); *B01L 3/0293* (2013.01); *B01L 3/5027* (2013.01); *G01N 1/28* (2013.01); *B01L 2200/12* (2013.01); *B01L 2300/0838* (2013.01); *B01L 2300/12* (2013.01); *B01L 2400/0406* (2013.01); *B01L 2400/0475* (2013.01); *B01L 2400/0677* (2013.01); *B01L 2400/0683* (2013.01); *G01N 1/38* (2013.01)

(58) Field of Classification Search
CPC ....................................... G01N 1/00
See application file for complete search history.

(56) References Cited

U.S. PATENT DOCUMENTS 3,475,127 A  10/1969  Gilford
3,630,191 A  12/1971  Gilford
3,811,326 A  5/1974  Sokol
(Continued)

OTHER PUBLICATIONS

International Search Report and Written Opinion of International Application No. PCT/US2015/035326 dated Nov. 4, 2015.
(Continued)

*Primary Examiner* — Jyoti Nagpaul
(74) *Attorney, Agent, or Firm* — Kyle D. Petaja

(57) ABSTRACT

Inventive concepts disclosed herein are directed to a capillary tube and a force assisted sample ejection mechanism. The capillary tube may be at least one of dissolvable or breakable. The force assisted sample ejecting mechanism releasing at least part of the sample of the first liquid from the capillary tube by at least one of abruptly shaking the capillary tube at least once or breaking the capillary tube.

10 Claims, 1 Drawing Sheet

(51) Int. Cl.
  *G01N 1/28* (2006.01)
  *G01N 1/38* (2006.01)

(56) References Cited

U.S. PATENT DOCUMENTS

| | | |
|---|---|---|
| 4,589,421 A | 5/1986 | Ullman |
| 4,866,097 A * | 9/1989 | Drake ................. A61K 9/2009 |
| | | 514/770 |
| 5,257,984 A | 11/1993 | Kelley |
| 6,102,896 A | 8/2000 | Roser |
| 6,368,356 B1 | 4/2002 | Zhong et al. |
| 7,488,604 B2 | 2/2009 | Clark et al. |
| 2002/0082522 A1 | 6/2002 | Douglas et al. |
| 2008/0081378 A1 | 4/2008 | Ramel |
| 2014/0017147 A1 | 1/2014 | Kim et al. |

OTHER PUBLICATIONS

European Search Report and Written Opinion of European Application No. 15805748.9 dated Aug. 10, 2017.
European Search Report of European Application No. 15805748.9 dated Apr. 7, 2017.
European Search Report and Written Opinion of European Application No. 18196227.5 dated Apr. 12, 2019.

* cited by examiner

SAMPLE DELIVERY SYSTEM

The subject application claims benefit under 35 USC § 119(e) of U.S. provisional Application No. 62/011,609, filed Jun. 13, 2014. The entire contents of the above-referenced patent application are hereby expressly incorporated herein by reference.

BACKGROUND

1. Field of the Disclosure

This disclosure relates to a device for faster sample delivery into a liquid medical assay.

2. Brief Description of the Related Art

In certain liquid based medical assay devices, a portion of a sample liquid to be tested is retained in a capillary tube. The capillary tube is then fully or partially submerged into a second liquid, such as an assay diluent (also known as an assay reaction solution). The portion of the sample liquid in the capillary tube then diffuses into the assay reaction solution. The diffusion of the portion of the sample liquid out of the capillary tube, however, is a relatively slow process.

SUMMARY OF THE INVENTIVE CONCEPT(S)

In one aspect, the inventive concepts disclosed herein are directed to a capillary tube and a force assisted sample ejection mechanism. The capillary tube absorbing and retaining a sample of a first liquid by capillary action when placed in contact with the first liquid. The capillary tube has a generally hollow tubular body that is open on one or both ends. The force assisted sample ejecting mechanism releasing at least part of the sample of the first liquid from the capillary tube when the sample of the first liquid is retained in the capillary tube. The force assisted sample ejecting mechanism releasing the sample of the first liquid by abruptly shaking the capillary tube at least once.

The inventive concepts disclosed herein are further directed to a capillary tube absorbing and retaining a sample of a first liquid by capillary action when placed in contact with the first liquid. The capillary tube has a generally hollow tubular body that is open on one or both ends. The capillary tube being made of a dissolvable polymer that dissolves when submerged in a second liquid.

The inventive concepts disclosed herein are additionally directed to a breakable capillary tube and a force assisted sample ejection mechanism. The breakable capillary tube absorbing and retaining a sample of a first liquid by capillary action when placed in contact with the first liquid. The breakable capillary tube having a generally hollow tubular body that is open on one or both ends. The force assisted sample ejection mechanism releasing at least part of the sample of the first liquid from the breakable capillary tube when the sample of the first liquid is retained in the breakable capillary tube. The force assisted sample ejection mechanism breaking the breakable capillary tube in order to release the first liquid.

BRIEF DESCRIPTIONS OF THE DRAWINGS

DETAILED DESCRIPTION OF THE INVENTIVE CONCEPT(S)

Figure 1:
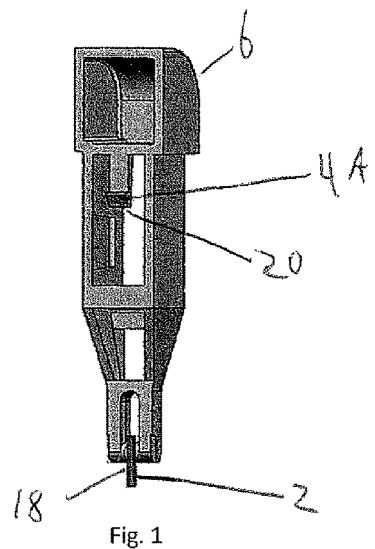
FIG. 1 illustrates one embodiment of a sample insertion device and a capillary tube.

Before explaining at least one embodiment of the inventive concepts disclosed herein in detail, it is to be understood that the inventive concepts are not limited in their application to the details of construction and the arrangement of the components or steps or methodologies set forth in the following description or illustrated in the drawings. The inventive concepts disclosed herein are capable of other embodiments or of being practiced or carried out in various ways. Also, it is to be understood that the phraseology and terminology employed herein is for the purpose of description and should not be regarded as limiting the inventive concepts disclosed and claimed herein in any way.

In the following detailed description of embodiments of the inventive concepts, numerous specific details are set forth in order to provide a more thorough understanding of the inventive concepts. However, it will be apparent to one of ordinary skill in the art that the inventive concepts within the instant disclosure may be practiced without these specific details. In other instances, well-known features have not been described in detail to avoid unnecessarily complicating the instant disclosure.

As used herein, the terms "comprises," "comprising," "includes," "including," "has," "having" or any other variation thereof, are intended to cover a non-exclusive inclusion. For example, a composition, a process, method, article, or apparatus that comprises a list of elements is not necessarily limited to only those elements but may include other elements not expressly listed or inherently present therein.

As used herein the terms "approximately," "about," "substantially" and variations thereof are intended to include not only the exact value qualified by the term, but to also include some slight deviations therefrom, such as deviations caused by measuring error, manufacturing tolerances, wear and tear on components or structures, settling or precipitation of cells or particles out of suspension or solution, chemical or biological degradation of solutions over time, stress exerted on structures, and combinations thereof, for example.

As used herein, the term "liquid sample" and variations thereof is intended to include, for example, but not limited to, biological fluids, chemical fluids, chemical substances, suspensions, solutions, slurries, mixtures, agglomerations, tinctures, slides, or other preparations of biological fluids, synthetic analogs to biological fluids, and combinations thereof.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present). An inclusive or may be understood as being the equivalent to: at least one of condition A or B.

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

The inventive concepts disclosed herein are generally directed to methods and devices for speeding up the delivery of the delivery of the sample liquid to be tested—housed in a capillary tube—into an assay reaction solution as part of a medical assay. The methods/devices disclosed herein involve, for example, shaking the contents of the capillary tube out into the assay reaction solution, utilizing a capillary tube that dissolves in a second liquid and/or breaking the capillary tube.

Figure 2:
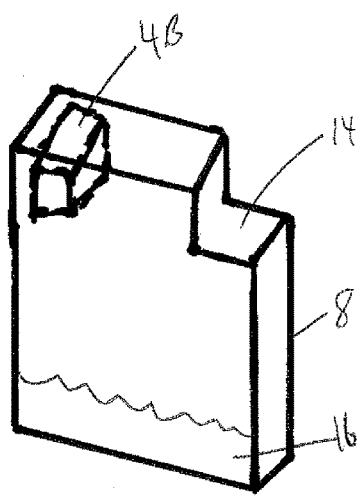
FIG. 2 illustrates one embodiment of a container.
Figure 3:
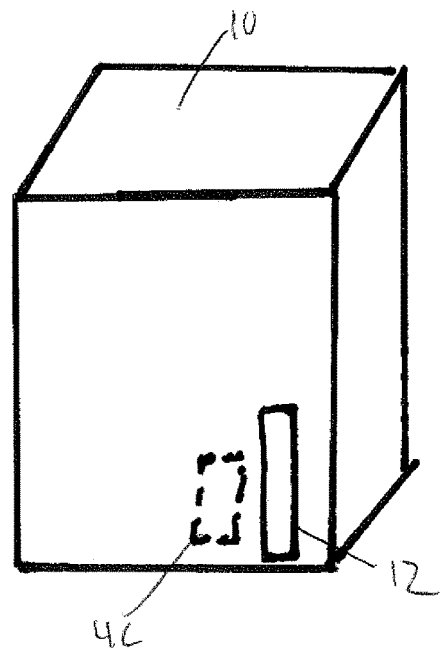
FIG. 3 illustrates one embodiment of a diagnostics device.

Referring to FIGS. 1-3, an exemplary capillary tube 2 is shown. The capillary tube 2 being able to absorb and retain a sample of a sample liquid 18 by capillary action. Sample liquid 18 may be any type of liquid. For example, sample liquid 18 may be a biological sample such as whole blood, plasma, serum, urine, saliva etc. . . . . In the example of whole blood, when placed in contact with the whole blood (such as when the capillary tube 2 is placed against a patient's finger after that finger has been pricked), a portion may be drawn into the capillary tube 2 by capillary action. The capillary tube 2 may be made out of a variety of materials such as, for example but not limited to, glass or plastic. The capillary tube 2 has a generally hollow tubular body that is open on one or both ends. The hollow tubular body of the capillary tube 2 may have a cross section resembling a variety of different geometric shapes (for example a triangle, circle, rectangle, pentagon, etc. . . . ).

During the medical assay procedure, the sample liquid 18 in capillary tube 2 is combined with a second liquid 16. Second liquid 16 may be an aqueous solution, such as a liquid assay diluent 16. Liquid assay diluent 16 may be retained in a container 8. Container 8 of FIG. 2 is intended to function as an example only. It should be appreciated that container 8 may take on a wide variety of shapes and sizes.

In an embodiment, the sample liquid in capillary tube 2 may be combined with the liquid assay diluent 16 in the container 8 by forcefully releasing all or at least part of sample liquid 18 into the liquid assay diluent 16 and/or container 8. A forceful release (which may also be referred to as splattering) of the sample liquid 18 may be accomplished by abruptly shaking the capillary tube 2 at least once via a force assisted sample ejecting mechanism 4. As depicted in FIGS. 1-3, one or more, or each, of a insertion device 6 (described in further detail below), the container 8, and a diagnostic device 10 may have a force assisted sample ejecting mechanism 4A, 4B, and 4C, respectively. One or more of force assisted sample ejecting mechanisms 4A, 4B, and 4C may function in tandem or separately in order to release the sample liquid 18 from the capillary tube 2. Diagnostic Device 10 may be configured to receive (via opening 12) the container 8 and interpret the assay results.

The force assisted sample ejecting mechanism 4 may operate by one or more of shaking the container 8 one or more times, shaking the capillary tube 2 one or more times, hitting the container 8 one or more times, hitting the capillary tube 2 one or more times, vibrating the container 8 one or more times, vibrating the capillary tube 2 one or more times, or using more force than is needed to place the insertion device 6 in the container 8. Accordingly the force assisted sample ejecting mechanism 4 may be located within the container 8 or outside of the container 8. The force assisted sample ejecting mechanism 4 may shake the capillary tube 2 but not the container 8 or the capillary tube 2 and the container 8.

Insertion device 6 may permanently or temporarily grip the capillary tube 2 and may be used to aid in the insertion of the capillary tube 2 into the container 8. Examples of insertion devices 6 may include, for example, tweezers, parallel groves between which the capillary tube 2 can be held in place, forceps, etc. Alternatively, the insertion device 6 may be integrated into the container 8 itself. In yet another alternative, the insertion device 6 may be used to simply drop the capillary tube 2 into the container 8. In the embodiment depicted in FIGS. 1-2, the insertion device 6 is inserted through opening 14 in container 8.

In the example depicted in FIG. 1, the capillary tube 2 is affixed to the sample insertion device 6. Once the capillary tube 2 has been loaded with sample liquid 18, the insertion device 6 may be inserted into container 8 such that the capillary tube 2 is placed in a test position within the container 8. In the test position, the capillary will be fully or partially submerged with the assay diluent 16 while the assay takes place. In an embodiment, the force assisted sample ejecting mechanism 4 is activated while placing the insertion device 6 in the container 8.

According to another embodiment of the invention, a method of releasing at least part of sample liquid includes abruptly shaking the capillary tube 2—which retains at least part of the sample liquid 18—at least once. The shaking motion being sufficient to result in the ejection of at least part of the first liquid from the capillary tube 2. When the capillary tube 2 is positioned above or within the container 8, the shaking motion involving: (1) shaking the capillary tube 2 but not a container 8 or (2) the capillary tube 2 and the container 8. The shaking may take place upon inserting the insertion device 6, to which the capillary tube is affixed, into the container 8 or after the insertion device 6 has been inserted. The container 8 may retain the assay diluent 16 prior to or after the shaking. For example, FIG. 1 depicts an insertion device 6 with a tab 20. When the insertion device 6 is inserted into container 8, the tab 20 may operate to with the housing of container 8 to shake the capillary tube 2 as the tab 20 passes into the housing. The size and rigidity of the tab 20 can be selected in order to optimize the shaking movement imparted onto the capillary tube 2 as the tab 20 engages the container 8.

In another embodiment of the invention, capillary tube 2 is dissolvable. The dissolvable capillary tube 2 may be utilized alone or in combination with the force assisted ejection mechanism 4. Dissolvable capillary tubes 2 are made of a dissolvable material, such as a polymer, wherein the dissoluble polymer dissolves when in contact with the assay diluent 16. Dissolvable capillary tube 2 may affixed to an insertion device 6 and inserted into the container 8 using the insertion device 6 or simply dropped into the container 8.

In order to prevent the capillary tube 2 from dissolving before it comes into contact with the assay diluent 16, the inside of the capillary tube 2 may have a coating which prevents the sample liquid 18 from dissolving the capillary tube 2 but does not prevent the sample liquid 18 from doing so. Alternatively, where the sample liquid 18 and the assay diluent 16 have different pH values, the capillary tube 2 may be composed of a material that is pH sensitive and dissolves in the assay diluent 16 but not the liquid sample 18. In the example where the sample liquid 18 is whole blood, the capillary tube 2 may be comprised of a polylactide which is not dissolved by whole blood (which has a near neutral pH) but in an assay diluent 16 having a higher or lower pH. This would cause the polymer to hydrolyze when the capillary tube 2 is at least partially submerged, thereby dissolving the capillary tube 2.

In another embodiment of the invention, capillary tube 2 is breakable. The breakable capillary tube 2 may also be dissolvable as disclosed above. When utilizing breakable capillary tubes 2, force assisted ejection mechanism 4 operates to break the breakable capillary tube 2 in order to release the first liquid. Breakable capillary tube 2 may be made out of any material that is breakable, such as glass, plastic, etc. . . . . . Breakable capillary tube 2 may affixed to an insertion device 6 and inserted into the container 8 using the insertion device 6 or simply dropped into the container 8. When using an insertion device 6, the force assisted sample ejection mechanism 4 may operate to break the capillary tube 2 during insertion into the container 8 or once the capillary tube 2 is positioned in the test position. Alternatively, capillary tube 2 may be dropped into the container 8 in order to break it or broken prior to being inserted into the cartridge.

As described above, the force assisted sample ejection mechanism 4 can be part of the insertion device 6 and/or the container 8 and can be located within the container 8 or outside of the container 8. In order to break a breakable capillary tube 2, the force assisted sample ejection mechanism 4 operates by at least one of breaking, hitting, crushing, shattering, piercing, or snapping the capillary tube 2 in a manner sufficient to break it into at least two pieces.

The following is a numbered list of non-limiting, illustrative embodiments of the inventive concepts disclosed herein:

1. A device, the device comprising: a capillary tube, the capillary tube absorbing and retaining a sample of a first liquid by capillary action when placed in contact with the first liquid, the capillary tube have a generally hollow tubular body that is open on one or both ends; and a force assisted sample ejecting mechanism, the force assisted sample ejecting mechanism releasing at least part of the sample of the first liquid from the capillary tube when the sample of the first liquid is retained in the capillary tube, the force assisted sample ejecting mechanism releasing the sample of the first liquid by abruptly shaking the capillary tube at least once.

2. The device of illustrative embodiment 1, further comprising a container to receive the sample of the first liquid and combine the sample of the first liquid with a second liquid.

3. The device of illustrative embodiment 2, wherein the force assisted sample ejection mechanism shakes the capillary tube but not the container.

4. The device of illustrative embodiment 2, wherein the force assisted sample ejection mechanism shakes the capillary tube and the container.

5. The device as in one of illustrative embodiments 1-4, further comprising an insertion device, the capillary tube being affixed to the insertion device, wherein when the insertion device is placed in the container and the insertion device cooperates to position the capillary tube in a test position.

6. The device of illustrative embodiment 5, in which the force assisted sample ejecting mechanism is part of the insertion device.

7. A device as in one of illustrative embodiments 2-6, in which the force assisted sample ejecting mechanism is located within the container.

8. The device as in one of illustrative embodiments 2-7, wherein the force assisted sample ejecting mechanism is part of the container.

9. A device as in one of illustrative embodiments 2-5, in which the force assisted sample ejecting mechanism is located outside of the container.

10. The device as in one of illustrative embodiments 2-9, wherein the force assisted sample ejecting mechanism is activated while placing the insertion device in the container.

11. The device of illustrative embodiment 10, wherein the force assisted sample ejecting mechanism operates by at least one of hitting the container, shaking the container, shaking the container and the capillary tube, or using more force than needed to place the insertion device in the container.

12. A method of releasing at least part of a first liquid retained in a capillary tube from the capillary tube, the method comprising: abruptly shaking a capillary tube at least once, the capillary tube retaining a first liquid by capillary action, the capillary tube have a generally hollow tubular body that is open on one or both ends, the shaking being sufficient to result in the ejection of at least part of the first liquid from the capillary tube.

13. The method of illustrative embodiment 12, in which shaking comprises shaking the capillary tube but not a container when the capillary tube is positioned above or within the container.

14. The method of illustrative embodiment 12, in which shaking comprises shaking the capillary tube and a container when the capillary tube is positioned above or within the container.

15. A method as in one of illustrative embodiments 12-14, further comprising: receiving an insertion device, to which the capillary tube has been affixed; and positioning the capillary tube in a test position.

16. The method of illustrative embodiment 15, in which the capillary tube is shaken while the capillary tube is positioned in the test position.

17. A method as in one of illustrative embodiments 12 through 16, in which shaking comprises one or more of hitting the container, hitting the capillary tube, shaking the container, shaking the container and the capillary tube, or using more force than needed to place the insertion device in the container.

18. A illustrative embodiment comprising: a capillary tube, the capillary tube absorbing and retaining a sample of a first liquid by capillary action when placed in contact with the first liquid, the capillary tube have a generally hollow tubular body that is open on one or both ends, the capillary tube being made of a dissolvable polymer, wherein the dissoluble polymer dissolves when submerged in a second liquid.

19. The device of illustrative embodiment 18, wherein the device is an assay device, the first liquid is whole blood, and the second liquid is an assay diluent.

20. A device of any of illustrative embodiments 18 or 19, further comprising a container to receive the sample of the first liquid and combine the sample of the first liquid with a second liquid.

21. The device of illustrative embodiment 20, wherein the capillary tube being affixed to the insertion device, wherein when the insertion device is placed in the container the capillary tube is at least partially submerged in the second liquid.

22. A device of any of illustrative embodiments 18-21, wherein the second liquid is an aqueous solution.

23. A method of releasing at least part of a first liquid retained in a capillary tube from the capillary tube, the method comprising: inserting a capillary tube in a second liquid, the capillary tube absorbing and retaining a sample of a first liquid by capillary action when placed in contact with the first liquid, the capillary tube have a generally hollow tubular body that is open on one or both ends, the capillary tube being made of a dissolvable polymer, wherein the dissoluble polymer dissolves when submerged in the second liquid.

24. A device comprising: a breakable capillary tube, the breakable capillary tube absorbing and retaining a sample of a first liquid by capillary action when placed in contact with the first liquid, the breakable capillary tube have a generally hollow tubular body that is open on one or both ends; a force assisted sample ejection mechanism, the force assisted sample ejection mechanism releasing at least part of the sample of the first liquid from the breakable capillary tube when the sample of the first liquid is retained in the breakable capillary tube, the force assisted sample ejection mechanism breaking the breakable capillary tube in order to release the first liquid.

25. The device of illustrative embodiment 24, further comprising a container able to retain the sample of the first liquid as well as a second liquid.

26. The device of illustrative embodiment 25, further comprising an insertion device, the breakable capillary tube being affixed to the insertion device, wherein when the insertion device is placed in the container the breakable capillary tube is placed in a test position, wherein the force assisted sample ejection mechanism breaks the breakable capillary tube once the breakable capillary tube is in the test position.

27. The device of illustrative embodiment 26, in which the force assisted sample ejection mechanism is part of the insertion device.

28. The device of illustrative embodiment 27, wherein the force assisted sample ejection mechanism is activated while placing the insertion device in the container.

29. A device as in one of illustrative embodiments 25-28, in which the force assisted sample ejection mechanism is located within the container.

30. A device as in one of illustrative embodiments 28-29, wherein the force assisted sample ejection mechanism is part of the container.

31. A device as in one of illustrative embodiments 25-28, in which the force assisted sample ejection mechanism is located outside of the container.

32. The device as in one of illustrative embodiments 24-31, wherein the force assisted sample ejection mechanism operates by at least one of breaking, hitting, crushing, shattering, piercing, or snapping the breakable capillary tube.

33. A method of releasing at least part of a first liquid retained in a capillary tube from the capillary tube, the method comprising: breaking a breakable capillary tube, the breakable capillary tube absorbing and retaining a sample of a first liquid by capillary action when placed in contact with the first liquid, the breakable capillary tube have a generally hollow tubular body that is open on one or both ends; wherein the breakable capillary tube is broken by a force assisted sample ejection mechanism, the force assisted sample ejection mechanism.

What is claimed is:

1. A device, the device comprising:
    a breakable capillary tube, the breakable capillary tube absorbing and retaining a sample of a first liquid by capillary action when placed in contact with the first liquid, the breakable capillary tube have a generally hollow tubular body that is open on one or both ends;
    a force assisted sample ejection mechanism, the force assisted sample ejection mechanism releasing at least part of the sample of the first liquid from the breakable capillary tube when the sample of the first liquid is retained in the breakable capillary tube, the force assisted sample ejection mechanism breaking the breakable capillary tube into at least two pieces in order to release the first liquid.

2. The device of claim 1, further comprising a container able to retain the sample of the first liquid as well as a second liquid.

3. The device of claim 2, further comprising an insertion device, the breakable capillary tube being affixed to the insertion device, wherein when the insertion device is placed in the container the breakable capillary tube is placed in a test position, wherein the force assisted sample ejection mechanism breaks the breakable capillary tube once the breakable capillary tube is in the test position.

4. The device of claim 3, in which the force assisted sample ejection mechanism is part of the insertion device.

5. The device of claim 4, wherein the force assisted sample ejection mechanism is activated while placing the insertion device in the container.

6. The device of claim 5, wherein the force assisted sample ejection mechanism is part of the container.

7. The device of claim 2, in which the force assisted sample ejection mechanism is located within the container.

8. The device of claim 2, in which the force assisted sample ejection mechanism is located outside of the container.

9. The device of claim 1, wherein the force assisted sample ejection mechanism operates by at least one of breaking, hitting, crushing, shattering, piercing, or snapping the breakable capillary tube.

10. A method of releasing at least part of a first liquid retained in a capillary tube from the capillary tube, the method comprising:
    breaking a breakable capillary tube, the breakable capillary tube absorbing and retaining a sample of a first liquid by capillary action when placed in contact with the first liquid, the breakable capillary tube have a generally hollow tubular body that is open on one or both ends;
    wherein the breakable capillary tube is broken into at least two pieces by a force assisted sample ejection mechanism.

* * * * *